United States Patent [19]

Tooley et al.

[11] Patent Number: 5,096,682
[45] Date of Patent: Mar. 17, 1992

[54] TRIALKYL ARSINE REMOVAL FROM FLUIDS

[75] Inventors: Patricia A. Tooley, Dickson, Tenn.; Ted H. Cymbaluk, Bartlesville, Okla.; Gerhard P. Nowack, Bartlesville, Okla.; Marvin M. Johnson, Bartlesville, Okla.

[73] Assignee: Phillips Petroleum Company, Bartlesville, Okla.

[21] Appl. No.: 686,066

[22] Filed: Apr. 16, 1991

[51] Int. Cl.$^5$ .................. B01D 53/14; B01D 53/04; C07C 7/12; C10L 3/10
[52] U.S. Cl. .................. 423/245.1; 423/210; 210/660; 208/253; 585/823
[58] Field of Search .................. 585/848, 823, 845; 423/245.2, 245.1, 210; 210/660; 208/253

[56] References Cited

U.S. PATENT DOCUMENTS

| | | | |
|---|---|---|---|
| 3,634,530 | 1/1972 | Bills | 585/848 |
| 3,647,840 | 3/1972 | Bills | 252/353 |
| 3,789,581 | 2/1974 | Carr et al. | 55/73 |
| 3,812,652 | 5/1974 | Carr et al. | 55/68 |
| 4,011,058 | 3/1977 | Johnson et al. | 423/246 |
| 4,025,574 | 5/1977 | Tabler et al. | 585/848 |
| 4,042,669 | 8/1977 | Johnson et al. | 423/246 |
| 4,048,387 | 9/1977 | Lahme et al. | 429/50 |
| 4,129,605 | 12/1978 | Tabler et al. | 585/259 |
| 4,398,052 | 8/1983 | Tabler et al. | 585/845 |
| 4,400,564 | 8/1983 | Johnson et al. | 585/845 |
| 4,462,896 | 7/1984 | KItigawa et al. | 208/253 |
| 4,532,115 | 7/1985 | Nishino et al. | 423/210 |
| 4,578,256 | 3/1986 | Nishino et al. | 423/210 |
| 4,593,148 | 6/1986 | Johnson et al. | 585/823 |
| 4,605,812 | 8/1986 | Nowack et al. | 585/845 |
| 4,675,309 | 6/1987 | Hirai et al. | 585/829 |
| 4,717,785 | 1/1988 | Paxson | 585/823 |
| 4,797,366 | 1/1989 | van Lookeren-Campagne | 435/264 |
| 4,839,029 | 6/1989 | Ichikawa et al. | 208/251 R |
| 4,877,920 | 10/1989 | Lush et al. | 585/823 |
| 4,992,620 | 2/1991 | Nowack et al. | 585/823 |

FOREIGN PATENT DOCUMENTS 121339 10/1984 European Pat. Off. ............ 423/210
60-68034 4/1985 Japan .

OTHER PUBLICATIONS

R. C. Weast, ed, "Handbook of Chemistry and Physics", 54th Ed. CRC Press: Cleveland (1973), p. C-123.

*Primary Examiner*—Michael Lewis
*Assistant Examiner*—Peter T. DiMauro
*Attorney, Agent, or Firm*—K. K. Brandes

[57] ABSTRACT

Trialkyl arsines (in particular trimethyl arsine) are removed from a fluid (e.g., a hydrocarbon-containing gas) by contacting the fluid with a sorbent material comprising at least one copper hydrocarbon sulfonate, preferably a copper salt of an aliphatic or aromatic sulfonic acid, or with a copper-exchanged, sulfonated styrene polymer.

21 Claims, No Drawings

TRIALKYL ARSINE REMOVAL FROM FLUIDS

BACKGROUND OF THE INVENTION

This invention relates to the removal of trialkyl arsines from fluids by means of solid sorbents. In another aspect, this invention relates to the removal of trialkyl arsines from gases, in particular hydrocarbon-containing gases.

Materials for adsorbing and/or absorbing unsubstituted arsine ($AsH_3$) are well known. However, many of these materials are ineffective for the sorption of trialkyl arsines, which may be present as undesirable impurities in natural gas streams produced at some well sites. The present invention provides a sorbent material which is effective for removing trialkyl arsines from fluids by sorption (i.e., adsorption and/or absorption).

SUMMARY OF THE INVENTION

It is an object of this invention to provide a process for removing trialkyl arsines from fluids. It is another object of this invention to provide a process for removing trialkyl arsines from gases, in particular hydrocarbon-containing gases. Other objects will become apparent from the detailed description of the invention and the appended claims.

In accordance with this invention, a process for at least partially removing trialkyl arsines from fluids comprises the step of contacting a fluid feed which contains at least one trialkyl arsine with a sorbent material comprising at least one copper hydrocarbonsulfonate, wherein said contacting is carried out at such contacting conditions as to obtain a fluid product having a lower trialkyl arsine content than said feed (with the spent sorbent material containing the portion of trialkyl arsine which has been removed from the feed). Preferably, the sorbent material is a copper salt of an aliphatic or aromatic sulfonic acid or a copper-exchanged, sulfonated styrene polymer.

DETAILED DESCRIPTION OF THE INVENTION

The term "trialkyl arsine", as used herein, refers to compounds having the general chemical formula of $R_3As$, wherein each R is a radical independently selected from among alkyl groups (straight and/or branched), preferably having 1-6 (more preferably 1-3) carbon atoms. Particularly preferred trialkyl arsines are trimethyl arsine, triethyl arsine, dimethyl ethyl arsine and diethyl methyl arsine.

Any suitable liquid or gaseous fluid stream which contains trialkyl arsine(s) can be used as feed in the process of this invention. Preferably, the feed is gaseous. Non-limiting examples of suitable feeds are: natural gas; gaseous petroleum fractions comprising paraffins and olefins containing 1-6 carbon atoms per molecule; and gaseous products from thermal and catalytic cracking of petroleum, shale oil or coal. Generally, the gases comprise methane, ethane, ethylene, propane, propylene, n-butane, isobutane, butenes; and the like. These gas streams can contain other impurities, such as hydrogen sulfide, carbonyl sulfide (COS), mercaptans, organic sulfides, mercury and/or compounds thereof, carbon monoxide, carbon dioxide, inert gases ($N_2$, He, Ne, Ar), and the like.

Other arsenic compounds may also be present in the fluid stream which is treated by the process of this invention, such as $AsH_3$, $RAsH_2$, $R_2AsH$, and the like, wherein R is an alkyl group, as defined above. It is also possible to have triphenyl arsine, dialkyl phenyl arsines, dialkyl cycloalkyl arsines, and the like present in the feed.

Generally, the total concentration of the trialkyl arsine(s) in the feed (preferably gaseous) is in the range of from about 1 ppb As (1 part by weight arsenic per billion parts by weight of feed) to about 0.1 weight-% As, preferably about 0.01-10 ppm As (0.01-10 parts by weight arsenic per million parts by weight of feed). The concentrations of the other impurities and the exact composition of the feed will widely vary from feedstock to feedstock.

The first type of effective sorbent material used in the process of this invention includes copper(I) salts and copper(II) salts of hydrocarbonsulfonic acids, in particular alkanesulfonic acids containing from 4 to 30 carbon atoms per molecule or aromatic sulfonic acids containing from 6–30 carbon atoms per molecule.

The alkanesulfonic acids useful in the practice of this invention can be straight chain or branched. Non-limiting examples of suitable alkanesulfonic acids include n-butanesulfonic acid, 2-ethyl-1-hexanesulfonic acid, 2-methylnonanesulfonic acid, dodecanesulfonic acid, 2-ethyl-5-n-octyldecanesulfonic acid, n-eicosanesulfonic acid, and mixtures thereof.

Non-limiting examples of aromatic sulfonic acids useful in the practice of this invention include benzenesulfonic acid, alkylbenzenesulfonic acids wherein the alkyl member contains from 1 to 16 carbon atoms, such as p-toluenesulfonic acid, p-dodecylbenzenesulfonic acid, p-hexadecylbenzenesulfonic acid, and the like, naphthalenesulfonic acid, phenolsulfonic acid, naphthosulfonic acids and halobenzenesulfonic acids, such a p-chlorobenzenesulfonic acid, p-bromobenzenesulfonic acid, and mixtures thereof. A presently preferred aromatic sulfonic acid is p-dodecylbenzene sulfonic acid. Commercially available mixtures of o-, m-, and p-dodecylbenzenesulfonic acid can be employed. Preferably, the mixture employed is predominantly (i.e., 84–90 mole percent) the para isomer.

Petroleum sulfonic acids which comprise various alkane sulfonic acids and aromatic sulfonic acids can also be used in the practice of this invention. Such petroleum sulfonic acids can be prepared by sulfonation, generally with an $SO_3/SO_2$ mixture, of a deasphalted solvent-refined petroleum fraction having a viscosity of about 140–720 SUS at 210° F., as is described in U.S. Pat. No. 4,398,052.

The preferred copper salts used as sorbents in the present invention are generally prepared by refluxing a solution of the sulfonic acid in an inert diluent, as hereinafter described, together with cuprous oxide or cupric oxide, with a provision for removing the water of reaction. The preparation is generally carried out in an oxygen-free inert atmosphere such as under nitrogen. The molar ratio of acid to copper is preferably about 1:1 for Cu(I) salts and about 2:1 for Cu(II) salts. The preparation is carried out for a time sufficient to substantially complete the reaction. The copper salts can, if desired, be separated from the diluent, such as by vacuum distillation.

The copper sulfonates can be utilized in any suitable hydrocarbon solvent such as olefinic and aromatic hydrocarbon solvents having from about 5 to about 15 carbon atoms to produce a solution or slurry of the sorbent material. Examples of suitable aromatic solvents include benzene, the alkyl derivatives of benzene, as for example, toluene, the xylenes, isopropyl benzene, 1,3,5-trimethylbenzene, hexamethylbenzene, halogen-substituted benzenes, polynuclear aromatic hydrocarbons such as naphthalene, methylnapthalenes and the like. Examples of suitable olefinic solvents include n-hexene-1, n-octene-1, n-decene-1 and the like. The aromatic solvents are presently more preferred because solutions of copper salts in aromatic solvents are generally more stable than solutions of copper salts in olefinic solvents. Generally, the concentration of the dissolved copper sulfonate(s) in solution is about 0.01-2 mole/l preferably about 0.03-1 mole/l.

The second type of effective sorbent material which can be used in the process of this invention include copper-exchanged, sulfonated polystyrene resins. The sulfonated polystyrene resins are commercially available as ion-exchange resins and can be prepared by sulfonation (e.g., with sulfuric acid or chlorosulfonic acid or sulfur trioxide) of the corresponding styrene polymer. These sulfonated styrene polymers may be sulfonated styrene homopolymers (generally having a weight-average molecular weight of about 10,000 to about 50,000) or sulfonated styrene copolymers, preferably copolymers of styrene and divinylbenzene (generally having a weight-average molecular weight of about 10,000 to about 50,000; and containing about 2-50 weight-%, preferably about 5-10 weight-%, divinylbenzene as comonomer). Generally, the molar ratio of sulfonic acid to monomer (styrene and/or vinylbenzene) in the sulfonated polystyrene generally is in the range of about 0.05:1 to about 1:1. Ion-exchange resins, as described above, are commercially available (generally as beads of about 15-50 mesh size) from Rohm and Haas, Philadelphia, PA (under the Amberlyst ® trademark, and from Dow Chemical Company, Midland, MI (under the Dowex ® trademark).

The ion-exchange of the resins with copper generally is done by contacting (preferably at about 50°-90° C.) a sulfonated polystyrene resin with a solution of a copper salt (preferably an aqueous solution of copper(II) chloride, or copper(II) nitrate or copper(II) sulfate, or copper(II) acetate, or mixtures thereof), followed by washing with a suitable solvent and drying. Generally, the copper-exchanged, sulfonated polystyrene resin contains about 2-20, preferably about 5-15, weight-% Cu.

Any suitable contacting conditions can be employed in the sorption process of this invention. Generally, the temperature in the contacting zone is in the range of from about $-20°$ to about 100° C., preferably about 20° to about 50° C. Generally, the pressure in the contacting zone is in the range of from about 1 to about 500 atm., preferably about 1 to about 70 atm. When a solid sorbent material is employed (in particular a Cu-exchanged sulfonated styrene polymer resin), the gas hourly space velocity of the gaseous feed in the contacting zone generally is in the range of from about 10 to about 20,000 volume of feed/volume of sorbent/hour, preferably about 1,000 to about 10,000 volume/volume/hour, measured at about 25° C./1 atm. When a dissolved sorbent (i.e., a solution of a copper salt of a sulfonic acid is employed (generally in a counter-current operation), the volume ratio of the gaseous feed to the liquid sorbent solution generally is in the range of from about 100:1 to about 3000:1 (preferably about 300:1 to about 1000:1). Generally, the contacting is continued until trialkyl arsine breakthrough occurs, i.e., when the treated product contains more trialkyl arsines than can be tolerated, such as about 20 ppb.

Treatment of the feed streams in accordance with the process of this invention can be carried out in any suitable manner. In one preferred embodiment a bed of a solid sorbent is placed as a fixed bed in a confined zone, and a fluid stream (preferably a gas) is passed therethrough in either upward or downward flow. Other suitable, yet less preferred methods of treatment include a fluidized operation in which the feed and the solid sorbent particles are maintained in a state of turbulence under hindered settling conditions in a confined zone, or moving bed operations in which the solid sorbent passes as a moving bed countercurrently to or concurrently with the feed, etc. In a fixed bed operation of a continuous process, the flow of fluid can be rotated between two or more sorbent beds with at least one being in regular operation, the other being in a regeneration mode. Continuous processes are preferred, but it is understood that batch type operations can be employed when desired. When a solution of a dissolved sorbent is employed, gaseous feed and liquid sorbent solution are generally contacted in a continuous countercurrent absorption column (well known to those skilled in the art) wherein the gaseous feed generally flows upward and the sorbent solution flows downward. It is also possible to sparge the gaseous feed through the sorbent solution so as to provide intimate contact between gas and sorbent.

It is within the scope of this invention to employ a combination of sorbents, such as a first bed (guard bed) of a supported CuO-ZnO material (described in U.S. Pat. No. 4,593,148) or PbO/$Al_2O_3$ for substantial removal of $AsH_3$ and/or $H_2S$ from the feed, and at least one subsequent downstream bed containing the sorbent material of this invention for absorbing trialkyl arsines. This multi-bed operation can be carried out in one reactor containing a layer of the supported CuO-ZnO material or PbO/$Al_2O_3$ (or any other known sorbent for $AsH_3$ and $H_2S$) and a downstream layer of a trialkyl arsine sorbent of this invention. Or the multi-bed operation can be carried out using two (or more) separate sorption reactors: a first reactor containing the supported CuO-ZnO material or PbO/$Al_2O_3$ (or any other known sorbent for $AsH_3$ and $H_2S$) and a second reactor containing the trialkyl arsine sorbent of this invention, wherein the feed passes through the first reactor and thereafter through the second reactor.

The process of this invention will be further illustrated by the following non-limiting examples.

EXAMPLE I

This example illustrates the preparation of a preferred sorbent material and the experimental setup for investigating the sorption of trimethyl arsine by this sorbent material.

10 grams of dry Amberlyst ® 15 beads (a sulfonated styrene/vinylbenzene copolymer resin having a bead size of about 15-50 mesh, a surface area of about 40-50 $m^2/g$, a porosity of 0.3-0.35 cc/cc, a bulk density of about 0.6 g/cc, and a hydrogen ion concentration of about 4.9 milliequivalents per gram; marketed by Rohm and Haas, Philadelphia, PA) were mixed with a solution of 10 grams of $CuSO_4 \cdot 5H_2O$ in 50 cc water. The mixture was heated at about 80° C. for about 20 minutes. The $Cu^{+2}$-exchanged resin was separated from the solution by filtration, extracted with toluene, and dried under vacuum conditions. This sorbent material contained about 11.1 weight-% Cu and had a BET/N₂ surface area of 35 m²/g.

A nitrogen gas stream was passed through a flask containing liquid trimethyl arsine (provided by Strem Chemicals, Inc.), which was cooled to about −78° C. by placing the flask in a dry ice/acetone mixture. The exiting gas stream, which contained N₂ and about 0.066 weight-% trimethyl arsine (TMA), was passed through a glass tube of about 7 mm diameter and about 12 cm length containing about 1 gram of the above-described sorbent material. The gas which exited from the absorption tube was passed through an aqueous solution of KMnO₄ and then to a flow meter. The flow rate of the gas was about 1800 cc/hour (equivalent to about 360 cc/cc sorbent/hour).

When TMA breakthrough occured (i.e., when the sorbent had reached its maximum TMA absorption capacity), the purple color of the KMnO₄ solution turned brownish. After TMA breakthrough had been detected, the flow of the trimethyl arsine containing gas stream was stopped, and a purge stream of pure nitrogen was passed through the sorbent material for about 15 hours so as to purge unabsorbed trimethyl arsine therefrom. The spent sorbent (containing absorbed/absorbed TMA) was analyzed for As. At the time of TMA breakthrough, the solid sorbent material had picked up As (as trimethyl arsine).

EXAMPLE II

This example illustrates the preparation of two copper sulfonates and their use for trimethyl arsine (TMA) absorption.

The first sorbent was a solution of copper(I) p-dodecylbenzenesulfonate (prepared substantially in accordance with the procedure of Example I of U.S. Pat. No. 4,400,564) in xylene. A chemical analysis of the solution showed that it contained about 0.8 weight-% Cu. A feed stream of N₂ and 0.066 mole-% TMA (described in Example I) was bubbled through this solution. TMA breakthrough occured after about 25 liters of the feed gas had been passed through the solution. A chemical analysis of the TMA-saturated sorbent solution revealed that 0.347 g As (as TMA) had been absorbed at TMA breakthrough.

A second sorbent was a solution of Cu(II) p-dodecylbenzene sulfonate in xylene, which had been prepared by heating 5.57 g CuO with 46.4 g p-dodecylbenzene sulfonic acid in xylene under reflux conditions, with formed water being continuously removed through the top of the condenser and collected in a Dean-Stark trap. After 31 liters of the N₂/TMA feed stream (described in Example I) had been bubbled through 40 cc of the Cu(II) p-dodecylbenzene sulfonate solution, TMA breakthrough occured. A chemical analysis revealed that this second sorbent solution had absorbed 0.989 g As (as TMA) at TMA breakthrough.

Reasonable variations and modifications which will be apparent to those skilled in the art, can be made within the scope of the disclosure and appended claims without departing from the scope of this invention.

That which is claimed is:

1. A process for at least partially removing trialkyl arsines from gases comprising the step of contacting a gaseous feed which contains at least one trialkyl arsine with a sorbent material comprising at least one copper salt of a hydrocarbonsulfonic acid; wherein said contacting is carried out at such contacting conditions as to obtain a product having a lower trialkyl arsine content than said feed, and wherein the content of said at least one trialkyl arsine in said feed is such as to provide a level of about 1 ppb to about 0.1 weight-% As.

2. A process in accordance with claim 1, wherein said feed is a hydrocarbon-containing gas.

3. A process in accordance with claim 1, wherein said trialkyl arsine has the chemical formula of $R_3As$ with each R being independently selected from the group consisting of alkyl groups containing 1–6 carbon atoms.

4. A process in accordance with claim 3, wherein said alkyl groups contain 1–3 carbon atoms.

5. A process in accordance with claim 1, wherein said at least one trialkyl arsine is selected from the group consisting of trimethyl arsine, triethyl arsine, dimethyl ethyl arsine and diethyl methyl arsine.

6. A process in accordance with claim 1, wherein said sorbent material is a solution of at least one copper(I) salt of a hydrocarbonsulfonic acid selected from the group consisting of alkanesulfonic acids containing from 4–30 carbon atoms per molecule and aromatic sulfonic acids containing 6–30 carbon atoms per molecule.

7. A process in accordance with claim 6, wherein said sorbent material is a solution of copper(I) p-dodecylbenzenesulfonate in an aromatic solvent.

8. A process in accordance with claim 1, wherein said sorbent material is a solution of at least one copper(II) salt of a hydrocarbon-sulfonic acid selected from the group consisting of alkanesulfonic acids containing from 4–30 carbon atoms per molecule and aromatic sulfonic acids containing 6–30 carbon atoms per molecule.

9. A process in accordance with claim 8, wherein said sorbent material is a solution of copper(II) p-dodecylbenzenesulfonate in an aromatic solvent.

10. A process in accordance with claim 1, wherein said sorbent material is a 0.01–2 molar solution of said at least one copper salt of a hydrocarbonsulfonic acid.

11. A process for at least partially removing trialkyl arsines from fluids comprising the step of contacting a fluid feed which contains at least one trialkyl arsine with a sorbent material comprising at least one copper-exchanged, sulfonated styrene polymer; wherein said contacting is carried out at such contacting conditions as to obtain a fluid product having a lower trialkyl arsine content than said feed, and wherein the content of said at least one trialkyl arsine in said feed is such as to provide a level of about 1 ppb to about 0.1 weight-% As.

12. A process in accordance with claim 11, wherein said sorbent material is a copper-exchanged, sulfonated copolymer of styrene and divinylbenzene.

13. A process in accordance with claim 12, wherein said copper-exchanged, sulfonated copolymer has a weight-average molecular weight of about 10,000 to about 50,000, and contains about 2–50 weight divinylbenzene as comonomer.

14. A process in accordance with claim 12, wherein said copper-exchanged sulfonated copolymer has been dried and contains about 2–20 weight-% copper.

15. A process in accordance with claim 1, wherein said contacting is carried out at a temperature of about −20° C. to about 100° C. and a pressure of about 1 to about 70 atm.

16. A process in accordance with claim 11, wherein said fluid feed is a gas.

17. A process in accordance with claim 11, wherein said fluid feed is a hydrocarbon-containing gas.

18. A process in accordance with claim 11, wherein said trialkyl arsine has the chemical formula of $R_3As$ with each R being independently selected from the group consisting of alkyl groups containing 1-6 carbon atoms.

19. A process in accordance with claim 18, wherein said alkyl groups contain 1-3 carbon atoms.

20. A process in accordance with claim 11, wherein said fluid feed is a gas and said at least one trialkyl arsine is selected from the group consisting of trimethyl arsine, triethyl arsine, dimethyl ethyl arsine and diethyl methyl arsine.

21. A process in accordance with claim 11, wherein said contacting is carried out at a temperature of about $-20°$ C. to about $100°$ C. and a pressure of about 1 to about 70 atm.

* * * * *